United States Patent
Lai et al.

(10) Patent No.: US 6,918,931 B2
(45) Date of Patent: Jul. 19, 2005

(54) PREPOLYMERS WITH YELLOW DYE MOIETY

(75) Inventors: Yu-Chin Lai, Pittsford, NY (US); Dominic V. Ruscio, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 88 days.

(21) Appl. No.: 10/657,639

(22) Filed: Sep. 8, 2003

(65) Prior Publication Data

US 2005/0054803 A1 Mar. 10, 2005

(51) Int. Cl.$^7$ .................................................. A61F 2/16
(52) U.S. Cl. .................... 623/6.6; 351/159; 351/160 R; 351/162; 264/1.1; 556/425; 556/443; 556/450; 556/453; 528/28; 525/100; 525/106
(58) Field of Search ................................ 556/425, 443, 556/450, 453; 528/28; 106/31.51, 31.52; 525/100, 106; 351/156, 160 R, 162; 264/1.1; 623/6.11, 6.12, 6.56, 6.6

(56) References Cited

U.S. PATENT DOCUMENTS

| | | | |
|---|---|---|---|
| 5,470,932 A | 11/1995 | Jinkerson | 526/312 |
| 5,528,322 A | 6/1996 | Jinkerson | 351/163 |
| 5,543,504 A | 8/1996 | Jinkerson | 534/856 |
| 5,662,707 A | 9/1997 | Jinkerson | 623/6 |
| 5,891,931 A | 4/1999 | Leboeuf et al. | 522/64 |
| 6,015,842 A | 1/2000 | LeBoeuf et al. | 522/64 |
| 6,353,069 B1 | 3/2002 | Freeman et al. | 526/319 |

FOREIGN PATENT DOCUMENTS

| | | |
|---|---|---|
| JP | 1293541 A2 * | 3/2000 |
| JP | 2000-89171 | 3/2000 |

OTHER PUBLICATIONS

Machine Translation, JP 2000–089171, Ichinohe, Mar. 31, 2000.*

* cited by examiner

*Primary Examiner*—David J. Buttner
*Assistant Examiner*—Christopher Keehan
(74) *Attorney, Agent, or Firm*—Toan P. Vo

(57) ABSTRACT

Yellow dye moiety-containing prepolymers with blue light absorbing priorities and methods for producing the same for use in the production of relatively high refractive index polymeric compositions are described herein. Polymeric compositions so produced are useful in the production of ophthalmic devices such as for example intraocular lenses and corneal inlays.

34 Claims, No Drawings

PREPOLYMERS WITH YELLOW DYE MOIETY

FIELD OF THE INVENTION

The present invention relates to high refractive index yellow dye moiety-containing prepolymers useful in the manufacture of biocompatible medical devices such as intraocular lenses. More particularly, the present invention relates to high refractive index yellow dye moiety-containing prepolymers having functional groups that aid in blocking blue light, useful in the manufacture of ophthalmic devices.

BACKGROUND OF THE INVENTION

Since the 1940's optical devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. Mazzocco, U.S. Pat. No. 4,573,998, discloses a deformable intraocular lens that can be rolled, folded or stretched to fit through a relatively small incision. The deformable lens is inserted while it is held in its distorted configuration, then released inside the chamber of the eye, whereupon the elastic property of the lens causes it to resume its molded shape. As suitable materials for the deformable lens, Mazzocco discloses polyurethane elastomers, silicone elastomers, hydrogel polymer compounds, organic or synthetic gel compounds and combinations thereof.

In recent years, blue light (400–500 nm) has been recognized as being potentially hazardous to the retina. Accordingly, yellow dyes to block blue light have been used in foldable intraocular lenses, in conjunction with ultraviolet light absorbers, to avoid potential damaging effects. Freeman et al., U.S. Pat. No. 6,353,069, disclose high refractive index copolymers comprising two or more acrylate and/or methacrylate monomers with aromatic groups. Ophthalmic devices made of the copolymers may also include colored dyes, such as the yellow dyes disclosed in U.S. Pat. No. 5,470,932. Such materials exhibit sufficient strength to allow devices made of them, such as intraocular lenses, to be folded or manipulated without fracturing.

Because of shortcomings in the properties of many soft, flexible materials used in the manufacture of ophthalmic devices, such as the formation of water vacuoles or "glistenings", and low refractive index, which requires a lens to be relatively thick in order to provide a lens of proper refractive power, new materials useful in the manufacture of ophthalmic devices are needed.

SUMMARY OF THE INVENTION

Soft, foldable, high refractive index, high elongation, polymeric compositions or silicone elastomers are prepared in accordance with the present invention through a copolymerization process using high refractive index prepolymers having blue light absorption capability. The subject prepolymers have a refractive index of at least 1.42 and more preferably a refractive index of at least 1.45. Prepolymers of the present invention have a structure generally represented by the Formula 1 below:

FORMULA 1

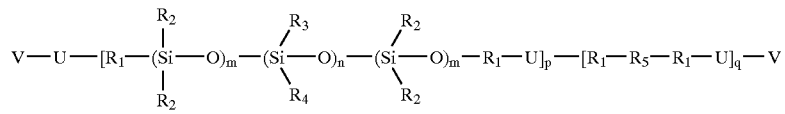

wherein the V groups may be the same or different reactive or polymerizable groups; the $R_1$ groups may be the same or different spacer groups, nothing or an organic spacing group; the $R_2$ groups may be the same or different $C_{1-6}$ alkyl groups; $R_3$ is either $R_2$ or $R_4$; $R_4$ is a $C_{6-30}$ aromatic group; $R_5$ is a yellow dye-containing moiety; the U groups may be the same or different difunctional linkage or nothing; and m, n, p and q represent the same or different non-negative integers greater than zero, with q being an integer such that the weight fraction of $R_5$ in the whole prepolymer is less than approximately 5 percent of the weight of the prepolymer and more preferably less than approximately 1 percent of the weight of the prepolymer.

Following preparation of the subject prepolymers using processes of the present invention described in more detail below, the prepolymers are copolymerized to form desirable polymeric compositions useful in the manufacture of biocompatible medical devices such as ophthalmic devices. Such desirable polymeric compositions are transparent, relatively high in elongation, relatively high in refractive index and particularly well suited for use in the manufacture of ophthalmic devices such as intraocular lens (IOL) implants, contact lenses, keratoprostheses, corneal rings, corneal inlays and the like. Medical devices fabricated from the polymeric compositions or silicone elastomers produced using prepolymers prepared in accordance with the present invention are also capable of absorbing blue light.

Accordingly, it is an object of the present invention to provide a process for the production of transparent, biocompatible polymeric compositions having desirable physical characteristics and relatively high refractive indices.

Another object of the present invention is to provide a process for the production of polymeric compositions having relatively high refractive indices and good clarity.

Another object of the present invention is to provide a process for the production of polymeric compositions suitable for use in the manufacture of ophthalmic devices.

Still another object of the present invention is to provide a process for the production of polymeric compositions suitable for use in the manufacture of intraocular lens implants.

These and other objectives and advantages of the present invention, some of which are specifically described and others that are not, will become apparent from the detailed description and claims that follow.

DETAILED DESCRIPTION OF THE INVENTION

The present invention relates to a novel process for the production of high refractive index prepolymers and the use of such prepolymers to produce biocompatible polymeric compositions having desirable physical properties and relatively high refractive indices for use in the manufacture of ophthalmic devices. The prepolymers of the present invention are represented generally by Formula 1 below:

represent the same or different non-negative integers greater than zero, with q being an integer such that the weight fraction of $R_5$ in the whole prepolymer is less than 5 percent of the weight of the prepolymer and more preferably less than 1 percent of the weight of the prepolymer.

The subject prepolymers of Formula 1 may be prepared using various techniques, depending on the specific prepolymer structure desired. In so doing, the amount of yellow dye moiety in the prepolymer can be easily controlled, depending on the level of blue light absorption capability desired, by adjusting the final formulation. Preferably, in accordance with the present invention, the polysiloxane portion of the prepolymer and the yellow dye moiety of the prepolymer are linked together through alkylene units or urethane, epoxy-amine, ester or carbonate linkages. Prepolymers, other than those linked together with alkylene units, can be prepared by first reacting a high refractive index α, ω-bis-hydroxyalkyl-terminated polysiloxane, diol-containing yellow dye compound with a diisocyanate, a diepoxy compound, a diacid chloride or the like in an appropriate molar (or weight) ratio to produce an isocyanate, an epoxy, an acid chloride or an alcohol end-capped prepolymer intermediate. The resultant end-capped prepolymer intermediate is then reacted with an ethylenically unsaturated monomer containing a functional group that reacts with the end-capped prepolymer intermediate to produce an ethylenically unsaturated prepolymer. This reactive ethylenically unsaturated compound used to

FORMULA 1

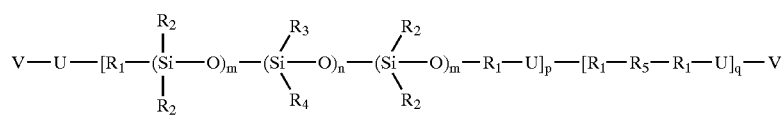

wherein the V groups may be the same or different reactive or polymerizable groups such as for example but not limited to vinyl, allyl, acrylate, methacrylate, acrylamide, methacrylamide, fumarate, maleate or styrene; the $R_1$ groups may be the same or different spacer groups such as for example but not limited to $C_{1-12}$ alkylene such as for example but not limited to propylene or butylene, nothing or an organic spacing group of up to 12 atoms in any combination such as but not limited to carbon, hydrogen, silicon, oxygen, nitrogen phosphorous, sulfur, chloride, bromine or fluorine; the $R_2$ groups may be the same or different $C_{1-6}$ alkyl groups such as for example but not limited to methyl, butyl or hexyl; $R_3$ is either $R_2$ or $R_4$; $R_4$ is a $C_{6-30}$ aromatic group such as for example but not limited to phenyl or naphthyl; $R_5$ is a yellow dye-containing moiety; the U groups may be the same or different difunctional linkage that renders the prepolymer with multiple blocks of polysiloxane groups and yellow dye groups such as for example but not limited to a urethane linkage, or nothing; and m, n, p and q end-cap the prepolymer may comprise for example but is not limited to hydroxylethyl methacrylate, hydroxyethyl acrylate, allyl alcohol, glycidal methacrylate, isocyanatoethyl methacrylate, allyl isocyanate, or the like. The ethylenically unsaturated prepolymer is then ready to copolymerize with comonomers through a vinyl polymerization or a hydrosilation reaction.

The structure of one specific prepolymer that can be prepared by the synthetic scheme just described is illustrated below in Formula 2.

FORMULA 2

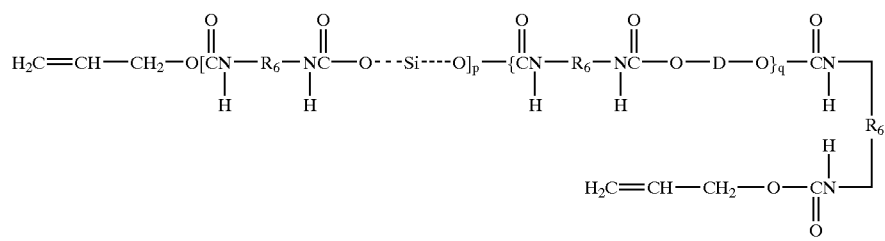

Here, $R_6$ is the residue from a diisocyanate after removing the two isocyanate groups; —SI— represents the α,ω-bishydroxy polysiloxane after removing the OH groups; D represents the dye compound after removing the two alcohol groups; and p and q are defined the same as previously defined above in Formula 1.

In accordance with the present invention, when the polysiloxane portion of a prepolymer and the yellow dye moiety of a prepolymer are linked together through alkylene linkages, the prepolymer can be prepared, for example, by a hydrosilation reaction of a dimethylhydrosiloxy-containing yellow dye compound with a divinyl-terminated high refractive index polysiloxane (in excess). One example of a prepolymer prepared in accordance with the reaction scheme just described is illustrated below in Formula 3.

$$H_2C=CH-SI-CH_2-CH_2-Si-D-Si-CH_2CH_2-SI-CH=CH_2 \quad \text{FORMULA 3}$$

Here, —SI— and D are defined the same as previously defined in Formula 2 above. Also, it should be noted that the amount of yellow dye moiety in the final polymeric composition is only an amount sufficient to block blue light. So, in making the prepolymer of Formula 3, only the required amount of yellow dye compound is used. As a result, prepolymers useful for the polymeric composition are most likely a mixture of prepolymers with and without yellow dye moieties.

Based on the particular molecular weights of the ingredients used in the synthesis of prepolymers of the present invention, the weight percent of yellow dye moiety present in the prepolymer can be calculated and thus the ultraviolet-visible (UV-VIS) transmittance determined. Through formulation studies with comonomers, the UV-VIS absorption of the final materials can be determined and can be adjusted as desired.

One class of yellow dye moiety-containing compounds particularly useful in the present invention are those containing two alcohol groups and the di-vinyl-containing derivatives thereof. One such example is N,N-bis-hydroxyethyl-(4'-phenylazo)aniline, known as Solvent Yellow 58, the structure of which is illustrated below in Formula 4.

FORMULA 4

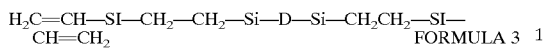

Another example is the dimethylhydrosiloxy derivative of Solvent Yellow 58, i.e., N-bis-(2-dimethylhydrosiloxyethyl)-(4-phenylazo)aniline, the structure of which is illustrated in Formula 5.

FORMULA 5

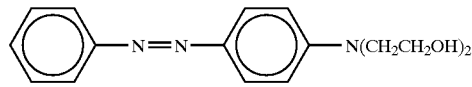

Depending on the nature of the V group of Formula 1, one or more prepolymers of the present invention can be copolymerized with one or more polymerizable monomers/oligomers through vinyl polymerization, stepwise addition, or hydrosilation to produce a polymer composition useful in the production of medical devices such as intraocular lenses. Blue-light absorbing functional groups should be present in such medical devices in an amount sufficient to provide approximately 50 percent or less light transmittance at 450 mn. The same is described in still greater detail in the Examples provided below.

EXAMPLE 1

Preparation of N,N-bis-hydroxyethyl-(4'-phenylazo) aniline

The synthesis of N,N-bis-(2-hydroxyethyl)-(4-phenylazo) aniline is accomplished by coupling the diazonium salt of aniline with N-phenyl diethanolamine. A detailed procedure is also described in D. L. Jinkerson, U.S. Pat. No. 5,470,932, incorporated herein in its entirety by reference.

EXAMPLE 2

Preparation of hydroxybutyl-terminated Copolymer of Dimethylsiloxane and Diphenylsiloxane (with 25 mole % Phenyl Content)

1,3-bis(hydroxybutyl)tetramethyl disilazane (33.70 g, 0.118 mole), dimethyldimethoxysilane (403.18 g, 3.25 moles) and diphenyldimethoxysilane (272.33 g, 1.08 moles) were added in a one-liter round bottom flask. Water (78.29 g) and concentrated hydrochloric acid (11.9 mL) were then slowly added to the flask. The contents of the flask were refluxed for one hour. Methanol (253.3 mL) was distilled from the contents. Water (160 mL) and concentrated hydrochloric acid (130 mL) was added to the flask. The contents of the flask were refluxed for one hour. The contents of the flask were then poured into a separatory funnel. The silicone layer was separated, diluted with 500 mL ether and washed once with 250 mL water, twice with 250 mL 5-percent sodium bicarbonate aqueous solution and twice with 250 mL water. The final organic layer was dried with magnesium sulfate, and then vacuum stripped at 80 degrees Celsius (0.1 mm Hg) to give the crude product. The crude product was then dissolved in 50/50 cyclohexane/methylene chloride and then passed through a silica gel column with the same solvent mixture. The final product was collected in tetrahydrofuran (THF) by passing THF through the silica gel column. The THF fractions were combined, dried and vacuum stripped to give the final product. Size Exclusion Chromatography (SEC) measurements of the final product indicated less than three percent cyclics and a molecular weight of 2821 by titration.

EXAMPLE 3

Preparation of Methacrylate-capped Prepolymer of Polysiloxane Containing Yellow Dye Moiety A 500-mL round bottom flask equipped with reflux condenser and nitrogen blanket is charged with isophorone diisocyanate (5.031 g, 0.0227 mole), the hydroxybutyl-terminated copolymer of dimethylsiloxane and the diphenylsiloxane from Example 2 (51.4465 g, 0.0189 mole), N,N-bis-hydroxyethyl-(4'-phenylazo)aniline (0.1730 g, 0.0006 mole), dibutyltin dilaurate (0.1811 g) and methylene chloride (150 mL). The flask contents are refluxed. After about 90 hours of reflux, the isocyanate is found decreased to about 15–20% percent of original. The contents of the flask is allowed to cool to ambient temperature. HEMA (1.1572 g) and 1,1'-2-bi-naphthol (5.7 mg) are added to the flask and stirred. After seven days, NCO peak disappears from IR spectrum and the reaction is terminated. The product is obtained at quantitative yield after removing solvent. This product contains 0.3% of yellow dye moiety.

EXAMPLE 4

Film Casting Studies

A mix consisting of the prepolymer of Example 3, benzyl acrylate, benzyl methacrylate and N,N,-dimethylacrylamide at a weight ratio of 50/20/10/20 is prepared. To the mix is added Lupersol 256™ (Atochem) at 1 percent of the total weigh. The mix is then cured between two silane-treated glass plates in an oven at 75° C. for 2 hours. The cured films are then released, extracted in isopropanol for over 4 hours and dried in a vacuum oven at 70° C. overnight. All dried films are then placed in a borate buffered saline overnight before characterization. Films of different thickness can be made in this manner. To mimic actual uses, films of 600 to 1000 microns in thickness should be made and the UV-VIS transmittance measured. With 0.15% by weight of dye moiety in the film, the UV-VIS transmittance should be less than approximately 50 to 60 percent at 450 nm.

EXAMPLE 5

Synthesis of Dimethylhydrosiloxy Derivative of N, N-bis-(2-dimethylhydrosiloxyethyl)-(4-phenylazo) aniline A 500-mL round bottom flask equipped with reflux condenser and nitrogen blanket is charged with 2.85 grams (0.01 mole) of N,N-bis-(2-hydroxyethyl)-(4-phenylazo)aniline and 300 mL of methylene chloride. The content is stirred at room temperature and added with 2.1 g (0.022 mole) dimethylhydrosilane (Gelest, Tulleytown, Pa.) in 10 mL of methylene chloride over period of 30 minutes through a dropping funnel. The stirring is continued for another 4 hours. The solvent is then stripped under vacuum to recover the product.

EXAMPLE 6

Preparation of Vinyl-terminated Polysiloxane with High Refractive Index and Yellow Dye Moiety Through Hydrosilation A 1000-mL round bottom flask equipped with reflux condenser and nitrogen blanket is charged with 0.205 grams (0.0005 mole) of N,N-bis-(2-dimethylhydrosiloxyethyl)-(4-phenylazo) aniline, 100 g of divinyl-terminated polydimethyl-co-diphenylsiloxane of Mn 30,000 (RI=1.43, Gelest, Inc., Tulleytown, Pa.) and 300 mL of methylene chloride. The content is stirred at room temperature and added with 10 mg of platinum divinyltetramethydisiloxane complex (2.1–2.4%) (Gelest, Inc) in 10 mL of methylene chloride. The content are heated to reflux and kept stirred for another 4 hours. The solvent is then stripped under vacuum to recover the product. This prepolymer would have 0.2% by weight of yellow dye moiety. And the prepolymer would have a refractive index at least 1.425.

EXAMPLE 7

Preparation of Polymeric Compositions Useful in the Manufacture of Intraocular Lenses Into a glass vial is charged with 1.4 g of prepolymer from Example 6, 0.4 gram of Q-resin (VQX-221, after removing xylene, Gelest, Tullytown, Pa.), 0.2 g of trimethysiloxane-terminated polydimethyl-comethylhydrosiloxane (HMS-501, Gelest Inc) and 15 mg of Pt-cyclovinylmethylsiloxane complex (Gelest, Inc) in 1,3-divinyltetramethydisloxane (1:10 ratio). The contents are stirred and then degassed to remove bubble (30 minutes). It is then poured between two stainless molds and then cured at 85° C. for 30 minutes. The lenses are then released from molds, extracted with isopropanol. The final lens has refractive index over 1.42, and block substantial amount of blue light depending on the thickness of lenses.

Soft, foldable, relatively high refractive index of approximately 1.42 or greater, relatively high elongation of approximately 100 percent or greater, polymeric compositions are synthesized using one or more yellow dye moiety-containing prepolymers of the present invention. To produce the subject polymeric compositions, one or more yellow dye moiety-containing prepolymers produced using the process of the present invention are copolymerized with one or more suitable monomers or oligomers and optionally one or more strengthening agents added to enhance the mechanical properties of the polymeric compositions, one or more crosslinking agents and/or one or more catalysts.

Suitable classes of polymerizable monomers or oligomers include for example but are not limited to high refractive index siloxane-containing acrylates, siloxane-containing methacrylates, aromatic-group-containing acrylates and aromatic-group-containing methacrylates. These monomers can copolymerize with acrylic/methacrylic end-capped prepolymers of the present invention through vinyl polymerization. On the other hand, vinyl- or allyl-containing siloxane monomers having high refractive indices, or vinyl or allyl-containing aromatic monomers can copolymerize with vinyl or allyl end-capped prepolymers of the present invention through hydrosilation with a Si—H containing polysiloxane.

Suitable strengthening agents for use in the copolymerization of the yellow dye moiety-containing allyl end-capped or vinyl end-capped prepolymer of the present invention includes but is not limited to silica filler or an organosilicon resin such as for example a Q-resin with multiple vinyl groups.

Suitable crosslinking agents for use in the copolymerization of the yellow dye moiety-containing vinyl end-capped prepolymer of the present invention include but are not limited to polydimethyl-co-methylhydrosiloxane.

Suitable catalysts for use in the copolymerization of the yellow dye moiety-containing vinyl end-capped prepolymer of the present invention includes but is not limited to Pt-silicone complex.

The polymeric compositions manufactured using yellow dye moiety-containing prepolymers of the present invention have refractive indices of approximately 1.42 or greater, relatively low glass transition temperatures of approximately 30 degrees Celsius or less and relatively high elongations of approximately 100 percent or greater. The polymeric compositions with the desirable physical properties described herein are particularly useful in the manufacture of ophthalmic devices such as but not limited to intraocular lenses (IOLs) and corneal inlays due to the capability of absorbing blue light.

IOLs having thin optic portions are critical in enabling a surgeon to minimize surgical incision size. Keeping the surgical incision size to a minimum reduces intraoperative trauma and postoperative complications. A thin IOL optic portion is also critical for accommodating certain anatomical locations in the eye such as the anterior chamber and the ciliary sulcus. IOLs may be placed in the anterior chamber for increasing visual acuity in both aphakic and phakic eyes and placed in the ciliary sulcus for increasing visual acuity in phakic eyes.

The polymeric compositions produced as described herein have the flexibility required to allow ophthalmic devices manufactured from the same to be folded or deformed for insertion into an eye through the smallest possible surgical incision, i.e., 3.5 mm or smaller. It is unexpected that the subject polymeric compositions described herein could possess the ideal physical properties disclosed herein. The ideal physical properties of the subject polymeric compositions are unexpected because high refractive index monomers or copolymers typically lend to polymers that have increased crystallinity and decreased clarity, which does not hold true in the case of the subject polymeric compositions.

One or more suitable ultraviolet light absorbers may optionally be used in the manufacture of the subject polymeric compositions. Such ultraviolet light absorbers include for example but are not limited to 2-[3'-tert-butyl-5'-(3"-dimethylvinylsilylpropoxy)-2'-hydroxyphenyl]-5-methoxybenzotriazole or 2-(3'-allyl-2'-hydroxy-5'-methylphenyl)benztriazole.

Medical devices produced using polymeric compositions produced using the process of the present invention may be manufactured in accordance with methods known to those skilled in the art of the specific ophthalmic device being produced. For example, if an intraocular lens is to be produced, the same may be manufactured by methods known to those skilled in the art of intraocular lens production.

Ophthalmic devices such as but not limited to IOLs and corneal inlays manufactured using polymeric compositions produced using the process of the present invention can be of any design capable of being rolled or folded for implantation through a relatively small surgical incision, i.e., 3.5 mm or less. For example, intraocular implants such as IOLs comprise an optic portion and one or more haptic portions. The optic portion reflects light onto the retina and the permanently attached haptic portions hold the optic portion in proper alignment within an eye following implantation. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOLs are made of the same polymeric composition produced using the process of the present invention. Alternatively however, the IOL optic portion and haptic portions may be manufactured from different materials and/or different formulations of polymeric compositions produced using the process of the present invention, such as described in detail in U.S. Pat. Nos. 5,217,491 and 5,326,506, each incorporated herein in their entirety by reference. Once the material(s) are selected, the same may be cast in molds of the desired shape, cured and removed from the molds. After such molding, the IOLs are then cleaned, polished, packaged and sterilized by customary methods known to those skilled in the art. Alternatively, rather than molding, the IOLs may be manufactured by casting said polymeric composition in the form of a rod; lathing or machining said rod into disks; and lathing or machining said disks into an ophthalmic device prior to cleaning, polishing, packaging and sterilizing the same.

In addition to IOLs, polymeric compositions produced using the prepolymers and processes of the present invention are also suitable for use in the production of other ophthalmic devices such as contact lenses, keratoprostheses, capsular bag extension rings, corneal inlays, corneal rings and like devices.

Ophthalmic devices manufactured using polymeric compositions produced using the prepolymers and processes of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While there is shown and described herein a process for producing yellow dye moiety-containing prepolymers, and polymeric compositions and ophthalmic devices made from the subject yellow dye moiety-containing prepolymers, it will be manifest to those skilled in the art that various modifications may be made without departing from the spirit and scope of the underlying inventive concept and that the same is not limited to particular processes and structures herein shown and described except insofar as indicated by the scope of the appended claims.

We claim:

1. Prepolymers comprising:

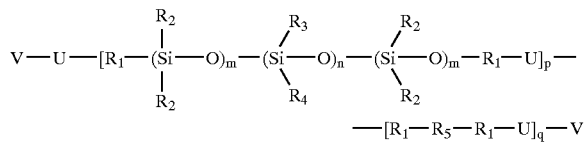

wherein the V groups may be the same or different reactive or polymerizable groups; the $R_1$ groups may be the same or different spacer groups, nothing or an organic spacing group; the $R_2$ groups may be the same or different $C_{1-6}$ alkyl groups; $R_3$ is either $R_2$ or $R_4$; $R_4$ is a $C_{6-30}$ aromatic group; $R_5$ is a yellow dye-containing moiety; the U groups may be the same or different difunctional linkage or nothing; and m, n, p and q represent the same or different non-negative integers greater than zero.

2. The prepolymer of claim 1 wherein q is an integer such that the weight of $R_5$ is less than approximately 5 percent of the weight of the prepolymer.

3. The prepolymer of claim 1 wherein q is an integer such that the weight of $R_5$ is less than approximately 1 percent of the weight of the prepolymer.

4. The prepolymer of claim 1 wherein said V groups are selected from the group consisting of vinyl, allyl, acrylate, methacrylate, acrylamide, methylacrylamide, fumarate, maleate and styrene.

5. The prepolymers of claim 1 wherein said $R_1$ groups are selected from the group consisting of spacer groups, nothing or an organic spacing group.

6. The prepolymers of claim 5 wherein said spacer groups are selected from the group consisting of $C_{1-12}$ alkylenes.

7. The prepolymers of claim 5 wherein said organic spacing group is composed of up to 12 atoms in any combination.

8. The prepolymers of claim 7 wherein said atoms are selected from the group consisting of carbon, hydrogen, silicon, oxygen, nitrogen, phosphorous, sulfur, chloride, bromine and fluorine.

9. The prepolymers of claim 1 wherein said $R_5$ group contains a yellow dye moiety.

10. The prepolymers of claim 1 wherein said U group is nothing or a difunctional linkage, which renders the prepolymer with multiple blocks of polysiloxane groups and yellow dye moieties.

11. The prepolymers of claim 1 wherein said U group is urethane.

12. The prepolymers of claim 1 wherein said prepolymers have blue light absorption properties.

13. A polymeric composition produced through the copolymerization of one or more prepolymers of claim 1 with one or more monomers or oligomers.

14. A polymeric composition produced through the copolymerization of one or more prepolymers of claim 1 with one or more monomers or oligomers, one or more strengthening agents, one or more crosslinking agents and one or more catalysts.

15. The polymeric composition of claim 13 or 14 wherein said one or more monomers or oligomers are selected from the group consisting of high refractive index siloxane-containing acrylates, high refractive index siloxane-containing methacrylates, aromatic-group-containing acrylates, aromatic-group-containing methacrylates, vinyl- or allyl-containing siloxane monomers having high refractive indices, and vinyl or allyl-containing aromatic monomers.

16. The polymeric composition of claim 14 wherein said strengthening agent is selected from a group consisting of a silica filler and a siloxane-based resin with at least one vinyl group.

17. The polymeric composition of claim 14 wherein said strengthening agent is a silica filler.

18. The polymeric composition of claim 14 wherein said strengthening agent is a siloxane-based resin with at least one vinyl groups.

19. The polymeric composition of claim 14 wherein said crosslinking agent is polydimethyl-co-methylhydrosiloxane.

20. The polymeric composition of claim 14 wherein said catalyst is a Pt-silicone complex.

21. The polymeric composition of claim 14 wherein said catalyst is Pt-silicone complex.

22. A process for producing the prepolymers of claim 1 comprising:

linking one or more yellow dye moiety-containing compounds with one or more polysiloxane compounds to produce a prepolymer intermediate; and reacting said prepolymer intermediate with an ethylenically unsaturated monomer containing a functional group.

23. A process for producing a polymeric composition comprising:

polymerizing one or more prepolymers of claim 1 with one or more monomers or oligomers.

24. A process for producing a polymeric composition comprising:

polymerizing one or more prepolymers of claim 1 with one or more monomers or oligomers, one or more strengthening agents, one or more crosslinking agents and one or more catalysts.

25. The process of claim 23 or 24 wherein said one or more monomers or oligomers are selected from the group consisting of high refractive index siloxane-containing acrylates, high refractive index siloxane-containing methacrylates, aromatic-group-containing acrylates, aromatic-group-containing methacrylates, vinyl- or allyl-containing siloxane monomers having high refractive indices, and vinyl or allyl-containing aromatic monomers.

26. The process of claim 24 wherein said reinforcing component is selected from a group consisting of silica filler or a siloxane-based-resin with at least one vinyl groups.

27. The process of claim 24 wherein said reinforcing component is a silica filler.

28. The process of claim 24 wherein said reinforcing component is a siloxane-based resin with at least one vinyl group.

29. A method of producing an ophthalmic device using the polymeric composition produced through the process of claim 23 or 24 comprising:

casting said polymeric composition into a shaped body.

30. A method of using the ophthalmic device produced through the method of claim 29 comprising:

implanting said ophthalmic device in an eye.

31. A method of producing an ophthalmic device using a polymeric composition produced from one or more of the prepolymers of claim 1 comprising:

casting said polymeric composition into a shaped body.

32. The method of using the ophthalmic device produced through the method of claim 31 comprising:

implanting said ophthalmic device in an eye.

33. A medical device containing one or more of the prepolymers of claim 1.

34. An intraocular lens containing one or more of the prepolymers of claim 1.

* * * * *